US008263100B2

(12) United States Patent
Areskoug et al.

(10) Patent No.: US 8,263,100 B2
(45) Date of Patent: Sep. 11, 2012

(54) SILVER-CONTAINING FOAM STRUCTURE

(75) Inventors: Stefan Areskoug, Molnlycke (SE); Ulf Johannison, Landvetter (SE); Malin Prydz, Stora Hoga (SE)

(73) Assignee: Mölnlycke Health Care AB, Göteborg (SE)

( * ) Notice: Subject to any disclaimer, the term of this patent is extended or adjusted under 35 U.S.C. 154(b) by 290 days.

(21) Appl. No.: 12/529,430

(22) PCT Filed: Feb. 13, 2008

(86) PCT No.: PCT/EP2008/001098
§ 371 (c)(1),
(2), (4) Date: Mar. 19, 2010

(87) PCT Pub. No.: WO2008/104276
PCT Pub. Date: Sep. 4, 2008

(65) Prior Publication Data
US 2010/0196501 A1  Aug. 5, 2010

(30) Foreign Application Priority Data

Mar. 1, 2007  (EP) .................................... 07004275

(51) Int. Cl.
*A01N 25/00* (2006.01)
*A01N 25/08* (2006.01)
*A01N 25/10* (2006.01)
*A01N 55/02* (2006.01)
*A01N 59/16* (2006.01)
*C08G 18/00* (2006.01)
*C08G 18/10* (2006.01)

(52) U.S. Cl. ........ 424/409; 424/405; 424/486; 424/618; 514/492; 514/495; 521/159; 521/160; 521/176; 521/905

(58) Field of Classification Search .................. 521/159, 521/160, 176, 905; 424/486, 618, 405, 409; 514/492, 495
See application file for complete search history.

(56) References Cited

U.S. PATENT DOCUMENTS

| | | | | |
|---|---|---|---|---|
| 3,536,638 A | * | 10/1970 | Dosmann | 521/75 |
| 4,137,200 A | * | 1/1979 | Wood et al. | 521/159 |
| 4,242,466 A | * | 12/1980 | Schilling et al. | 521/112 |
| 4,937,273 A | | 6/1990 | Okuyama | |
| 5,352,508 A | | 10/1994 | Cheong | |
| 5,607,683 A | * | 3/1997 | Capelli | 424/405 |
| 5,662,913 A | | 9/1997 | Capelli | |
| 5,681,575 A | | 10/1997 | Burrell | |
| 5,837,275 A | | 11/1998 | Burrell | |
| 6,051,747 A | | 4/2000 | Lindqvist et al. | |
| 6,207,875 B1 | | 3/2001 | Lindqvist et al. | |
| 6,375,964 B1 | * | 4/2002 | Cornelius | 424/404 |
| 2005/0037058 A1 | | 2/2005 | Canada | |
| 2005/0123621 A1 | | 6/2005 | Burton | |
| 2006/0029675 A1 | | 2/2006 | Ginther | |
| 2006/0234899 A1 | * | 10/2006 | Nekmard et al. | 510/439 |
| 2010/0021514 A1 | * | 1/2010 | Fugmann | 424/409 |
| 2010/0034882 A1 | * | 2/2010 | Gibbins et al. | 424/486 |
| 2010/0286584 A1 | | 11/2010 | Areskoug et al. | |
| 2011/0028919 A1 | | 2/2011 | Johnnison et al. | |

FOREIGN PATENT DOCUMENTS

| | | |
|---|---|---|
| EP | 0059049 | 9/1982 |
| EP | 1486523 | 12/2004 |
| WO | 9742985 | 11/1997 |
| WO | 02062403 | 8/2002 |
| WO | 03097727 | 11/2003 |
| WO | 2004007595 | 1/2004 |

OTHER PUBLICATIONS

Written Opinion issued on Mar. 20, 2008 for Intl. App. No. PCT/EP2008/001098, filed on Feb. 13, 2008 (Inventor—Areskoug et al.; Applicant—Molnlycke Health Care AB; pp. 1-7).
Preliminary Report on Patentability issued on May 22, 2009 for Intl. App. No. PCT/EP2008/001098, filed on Feb. 13, 2008 (Inventor—Areskoug et al.; Applicant—Molnlycke Health Care AB; pp. 1-9).
PACER Listing of Docket Entries, Nov. 29, 2010.
Stipulation of Dismissal; Sep. 16, 2008.
Deposition of Stephen J. Clarson, Ph.D.; Feb. 1, 2007.
Deposition of Stephen J. Clarson, Ph.D.; Mar. 6, 2008.
Markman Order; Jun. 21, 2007.
First Amended Complaint and Demand for Jury Trial; Jun. 15, 2006.
Preliminary Constructions of Defendants Medline Industries, Inc. and Ossur Hf; Dec. 21, 2006.
Joint Claim Construction Statement; Jan. 16, 2007.
Exhibit A of Joint Claim Construction Statement—Parties' proposed constructions of each disputed claim term, phrase, or clause and support for such constructions; Jan. 16, 2007.
Exhibit B of Joint Claim Construction Statement—Summary of Opinions of Dr. Stephen J. Clarson; Jan. 16, 2007.
Claim Constructing Brief of Defendants Medline Industries, Inc. and Ossur Hf; Feb. 7, 2007.
Molnlycke Health Care AB and Molnlycke Health Care US Opening Claim Construction Brief; Feb. 7, 2007.
Exhibit 1 of Molnlycke Health Care AB and Molnlycke Health Care US Opening Claim Construction Brief—U.S. Patent No. 6,051,747; Feb. 7, 2007.
Exhibit 2, Parts A-I of Molnlycke Health Care AB and Molnlycke Health Care US Opening Claim Construction Brief—Gentleheal® Marketing Materials; Feb. 7, 2007.

(Continued)

*Primary Examiner* — James H. Alstrum-Acevedo
(74) *Attorney, Agent, or Firm* — Ballard Spahr LLP (57) ABSTRACT

A method of producing a hydrophilic polyurethane foam structure containing a silver salt, chosen from the group of silver sulphate, silver citrate, silver acetate, silver carbonate, silver lactate and silver phosphate, or a mixture of these salts includes the steps of (a) providing a water phase containing a surfactant, and at least one silver salt, wherein the at least one silver salt is dispersed in the water phase; (b) providing a isocyanate-terminated polyether having functionality of more than (2); (c) mixing the water phase and the isocyanate-terminated polyether, immediately transferring the resulting mixture to a mould whereby a foam structure is obtained; and (d) drying the foam structure until it has a moisture content of at most 10% (wt). The hydrophilic polyurethane foam structure produced by the method and a wound dressing containing the foam structure are also described.

7 Claims, 8 Drawing Sheets

OTHER PUBLICATIONS

Exhibit 3 of Molnlycke Health Care AB and Molnlycke Health Care US Opening Claim Construction Brief—Excerpts of Technical Dictionaries in the Chemical and Medical Fields; Feb. 7, 2007.
Exhibit 4 Parts A-E of Molnlycke Health Care AB and Molnlycke Health Care US Opening Claim Construction Brief—Excerpts of General purpose dictionaries; Feb. 7, 2007.
Exhibit 5 Parts A-B of Molnlycke Health Care AB and Molnlycke Health Care US Opening Claim Construction Brief—U.S. Patent No. 7,154,017; Feb. 7, 2007.
Excerpts of Videotaped Deposition of Dr. Steven J. Clarson; Feb. 7, 2007.
Excerpts of Videotaped Deposition of Tomas T. Fabo; Feb. 7, 2007.
Responsive Claim Construction Brief of Defendants Medline Industries, Inc. and Ossur HF; Feb. 7, 2007.
Molnlycke Health Care AB and Molnlycke Health Care US Response to Medline Industries, Inc. and Ossur HF Opening Claim Construction Brief; Feb. 7, 2007.
Order; Jun. 21, 2007.
Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order; Nov. 5, 2007.
Exhibit A of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—U.S. Patent No. 6,051,747; Nov. 5, 2007.
Exhibit B of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Defendants Medline Industries, Inc. and Ossur HF Disclosure of Invalidity Contentions; Nov. 5, 2007.
Exhibit C of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Jan. 31, 2007 Videotaped Deposition of Tomas T. Fabo; Nov. 5, 2007.
Exhibit D of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Aug. 21, 2007 Videotaped Deposition of Tomas T. Fabo; Nov. 5, 2007.
Exhibit E of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Correspondence dated Oct. 8, 2007 from Mr. Baldassare Vinti to Mr. Steve Moore; Nov. 5, 2007.
Exhibit F of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Jul. 25, 2007 Hearing; Nov. 5, 2007.
Exhibit G of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Defendants' Objections and Responses to Plaintiffs' First Set of Continuing Interrogatories; Nov. 5, 2007.
Exhibit H of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Order—Excerpts of Transcript of Sep. 6, 2007 Deposition of Jonathan Primer; Nov. 5, 2007.
Exhibit I of Molnlycke Health Care AB and Molnlycke Health Care US Consolidated Brief in Opposition to Defendants Medline Industries, Inc. and Ossur HF Cross-Motion to Amend and in Reply to Defendants Opposition to Motion for Protective Orde—Excerpts of Transcript of Sep. 27, 2007 Deposition of Hilmar Jannusson; Nov. 5, 2007.
Exhibit J of Molnlycke Health Care Ab and Molnlycke Health Care US Consolidated Brief in Opposition to Defendants Medline Industries, Inc. and Ossur HF Cross-Motion to Amend and in Reply to Defendants Opposition to Motion for Protective Order—Plaintiffs' Objections to Notice of 30(b)(6) Depositions Concerning the Issues of Infringement, Validity, and Enforceability; Nov. 5, 2007.
Medline Industries, Inc. and Ossur HF Motion for Summary Judgment of Invalidity; Mar. 26, 2008.
Medline Industries, Inc. and Ossur HF Memorandum of Law in Support of Motion for Summary Judgment of Invalidity; Mar. 26, 2008.
Medline Industries, Inc. and Ossur HF Rule 56.1 Statement of Undisputed Material Facts; Mar. 26, 2008.
Declaration of Jennifer R. Scullion in Support of Medline Industries, Inc. and Ossur HF Motion for Summary Judgment of Invalidity; Mar. 26, 2008.
Exhibit a of Medline Industries, Inc. and Ossur HF Rule 56.1 Statement of Undisputed Material Facts—U.S. Patent No. 6,051,747; Mar. 26, 2008.
Exhibit B of Medline Industries, Inc. and Ossur HF Rule 56.1 Statement of Undisputed Material Facts—U.S. Patent No. 4,921,704; Mar. 26, 2008.
Exhibit C of Medline Industries, Inc. And Ossur HF Rule 56.1 Statement of Undisputed Material Facts—U.S. Patent No. 5,340,363; Mar. 26, 2008.
Exhibit D of Medline Industries, Inc. and Ossur HF Rule 56.1 Statement of Undisputed Material Facts—EP Patent No. 0 261 167; Mar. 26, 2008.
Exhibit E of Medline Industries, Inc. and Ossur HF Rule 56.1 Statement of Undisputed Material Facts—U.S. Patent No. 5,540,922; Mar. 26, 2008.
Exhibit F of Medline Industries, Inc. and Ossur HF Rule 56.1 Statement of Undisputed Material Facts—U.S. Patent No. 5,635,201; Mar. 26, 2008.
Exhibit G of Medline Industries, Inc. and Ossur Hf Rule 56.1 Statement of Undisputed Material Facts—British Patent No. 898,826; Mar. 26, 2008.
Exhibit H of Medline Industries, Inc. and Ossur Hf Rule 56.1 Statement of Undisputed Material Facts—Excerpts of Jan. 31, 2007 Videotaped Deposition of Tomas T. Fabo; Mar. 26, 2008.
Exhibit I of Medline Industries, Inc. and Ossur HF Rule 56.1 Statement of Undisputed Material Facts—Excerpts of Aug. 21, 2007 Videotaped Deposition of Tomas T. Fabo; Mar. 26, 2008.
MM48 Exhibit J of Medline Industries, Inc. and Ossur HF Rule 56.1 Statement of Undisputed Material Facts—Excerpts of Videotaped Deposition of Dr. Steven J. Clarson; Mar. 26, 2008.
Exhibit K of Medline Industries, Inc. and Ossur HF Rule 56.1 Statement of Undisputed Material Facts—Excerpts of Videotaped Deposition of Craig Broussard, Ph.D., R.N; Mar. 26, 2008.
Exhibit L of Medline Industries, Inc. and Ossur HF Rule 56.1 Statement of Undisputed Material Facts—Excerpts of Videotaped Deposition of Larry Bogart; v, Jan. 29 , 2008.
Exhibit M of Medline Industries, Inc. and Ossur HF Rule 56.1 Statement of Undisputed Material Facts—Excerpts of the Prosecution File of U.S. Patent No. 6,051,747; Mar. 26, 2008.
Exhibit N of Medline Industries, Inc. and Ossur HF Rule 56.1 Statement of Undisputed Material Facts—Excerpts of the Prosecution File of U.S. Patent No. 6,051,747; Mar. 26, 2008.
Exhibit O of Medline Industries, Inc. and Ossur HF Rule 56.1 Statement of Undisputed Material Facts—Excerpts of the Prosecution File of U.S. Patent No. 6,051,747; Mar. 26, 2008.
Exhibit P of Medline Industries, Inc. and Ossur HF Rule 56.1 Statement of Undisputed Material Facts—Excerpts of the Prosecution File of U.S. Patent No. 6,051,747; Mar. 26, 2008.
Exhibit Q of Medline Industries, Inc. and Ossur HF Rule 56.1 Statement of Undisputed Material Facts—Initial Memorandum of the Fabo Interference Proceeding; Mar. 26, 2008.
Exhibit R of Medline Industries, Inc. and Ossur HF Rule 56.1 Statement of Undisputed Material Facts—Sua Sponte Holding of Unpatentability in View of Prior Art; Mar. 26, 2008.

Exhibit S of Medline Industries, Inc. and Ossur HF Rule 56.1 Statement of Undisputed Material Facts—Molnlycke Health Care AB and Molnlycke Health Care US Supplemental Answers to Defendant Ossur HF's First Set of Interrogatories; Mar. 26, 2008.
Exhibit T of Medline Industries, Inc. and Ossur HF Rule 56.1 Statement of Undisputed Material Facts—Molnlycke Health Care AB and Molnlycke Health Care US Response to Medline Industries, Inc. and Ossur HF Claim Construction Brief; Mar. 26, 2008.
Expert Declaration of Dr. Michael A. Brook in Support of Medline Industries, Inc. and Ossur HF Motion for Summary Judgment; Mar. 26, 2008.
Exhibit A of Expert Declaration of Dr. Michael A. Brook in Support of Medline Industries, Inc. and Ossur HF Motion for Summary Judgment—Curriculum Vitae; Mar. 26, 2008.
Exhibit B of Expert Declaration of Dr. Michael A. Brook in Support of Medline Industries, Inc. and Ossur HF Motion for Summary Judgment—Expert Report of Michael A. Brook, Ph. D. on Validity Issues; Mar. 26, 2008.
Molnlycke Health Care AB and Molnlycke Health Care US Motion for Partial Summary Judgment That U.S. Patent 6,051,747 is Not Invalid; Mar. 26, 2008.
Placeholder for Brief in Support of Molnlycke Health Care AB and Molnlycke Health Care US Motion for Partial Summary Judgment That U.S. Patent 6,051,747 is Not Invalid Filed Under Seal Pursuant to Revised Protective Order Submitted to the Court on Sep. 21, 2007; Mar. 26, 2008.
Molnlycke Health Care AB and Molnlycke Health Care US Statement of Undisputed Material Facts in Support of Motion to Strike Medline Industries, Inc. and Ossur HF New and Untimely Non-infringing Alternative Theory, Including Exhibits 1-9 Filed Under Seal Pursuant to Revised Protective Order; Mar. 26, 2008.
Excerpts of Videotaped Deposition of Andrew Martin Reed, Ph.D.; Mar. 26, 2008.
Excerpts of Videotaped Deposition of Laura Shafer; Mar. 26, 2008.
Excerpts of Videotaped Deposition of Craig Broussard, Ph.D., R.N; Mar. 26, 2008.
Excerpts of Videotaped Deposition of Larry Bogart; Mar. 26, 2008.
Placeholder for Exhibit 6—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 7—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 8—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Excerpts of Jan. 31, 2007 Videotaped Deposition of Tomas T. Fabo; Mar. 26, 2008.
Placeholder for Exhibit 10—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 11—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 12—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 13—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 14—Molnlycke Health Care AB and Molnlycke Health Care US Motion for Partial Summary Judgment That U.S. Patent 6,051,747 is Not Invalid; Confidential—Filed . Under Seal Pursuant to Revised Protective Order Submitted to the Court on Sep. 21, 2007; Mar. 26, 2008.
Placeholder for Exhibit 15—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 16—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Excerpts of Videotaped Deposition of James Wetrich; Mar. 26, 2008.
Placeholder for Exhibit 18—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 19—Molnlycke Health Care Ab and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Placeholder for Exhibit 20—Molnlycke Health Care AB and Molnlycke Health Care US Motion for Partial Summary Judgment That U.S. Patent 6,051,747 is Not Invalid; Confidential—Filed Under Seal Pursuant to Revised Protective Order Submitted to the Court on Sep. 21, 2007; Mar. 26, 2008.
Excerpts of Deposition of Michael Brook; Mar. 26, 2008.
Molnlycke Health Care AB and Molnlycke Health Care US Brief in Opposition to Medline Industries, Inc. and Ossur HF Motion for Summary Judgment of Invalidity Apr. 24, 2008.
Exhibit 23 of Molnlycke Health Care AB and Molnlycke Health Care US Brief in Opposition to Medline Industries, Inc. and Ossur HF Motion for Summary Judgment of Invalidity—Excerpts of videotaped deposition of Andrew Martin Reed, Ph. D.; Apr. 24, 2008.
Exhibit 24 of Molnlycke Health Care AB and Molnlycke Health Care US Brief in Opposition to Medline Industries, Inc. and Ossur HF Motion for Summary Judgment of Invalidity—Excerpts of Deposition of Michael Brook; Apr. 24, 2008.
Exhibit 25 of Molnlycke Health Care AB and Molnlycke Health Care US Brief in Opposition to Medline Industries, Inc. and Ossur HF Motion for Summary Judgment of Invalidity—Excerpts of Videotaped Deposition of Dr. Steven J. Clarson; Apr. 24, 2008.
Exhibit 26 of Molnlycke Health Care AB and Molnlycke Health Care US Brief in Opposition to Medline Industries, Inc. and Ossur HF Motion for Summary Judgment of Invalidity—Excerpts of Videotaped Deposition of Larry Bogart; Apr. 24, 2008.
Exhibit 27 of Molnlycke Health Care AB and Molnlycke Health Care US Brief in Opposition to Medline Industries, Inc. and Ossur HF Motion for Summary Judgment of Invalidity—Excerpts of Deposition of Benoit Castel; Apr. 24, 2008.
Exhibit 28 of Molnlycke Health Care AB and Molnlycke Health Care US Brief in Opposition to Medline Industries, Inc. and Ossur HF Motion for Summary Judgment of Invalidity—*OrthoMcNeil Pharm., Inc* v. *Mylan Labs.,Inc.*, No. 2007-1223, 2008 WL 834402, at *5 (Fed. Cir. Mar. 31, 2008); Apr. 24, 2008.
Exhibit 29 of Molnlycke Health Care AB and Molnlycke Health Care US Brief in Opposition to Medline Industries, Inc. and Ossur HF Motion for Summary Judgment of Invalidity—Excerpts of Jan. 31, 2007 Videotaped Deposition of Tomas T. Fabo; Apr. 24, 2008.
Exhibit 30 of Molnlycke Health Care AB and Molnlycke Health Care US Brief in Opposition to Medline Industries, Inc. and Ossur HF Motion for Summary Judgment of Invalidity—Excerpts of Videotaped Deposition of Craig Broussard, Ph.D., R.N; Apr. 24, 2008.
Exhibit 31 of Molnlycke Health Care AB and Molnlycke Health Care US Brief in Opposition to Medline Industries, Inc. and Ossur HF Motion for Summary Judgment of Invalidity—Excerpts of the Prosecution File of U.S. Patent No. 6,051,747; Apr. 24, 2008.
Declaration of Stephen J. Clarson, Ph.D.; Apr. 24, 2008.
Declaration of Tomas Fabo dated Apr. 24, 2008; Apr. 24, 2008.
Exhibit A of Declaration of Tomas Fabo—Sua Sponte Holding of Unpatentability in View of Prior Art; Apr. 24, 2008.
Exhibit B of Declaration of Tomas Fabo—Fabo Opposition to the Sua Sponte Holding of Unpatentability in View of Prior Art; Apr. 24, 2008.
Exhibit C of Declaration of Tomas Fabo—Declaration of Tomas Fabo dated Oct. 30, 1991; Apr. 24, 2008.
Exhibit D of Declaration of Tomas Fabo—Opinion on the Final Hearing before the Board of Patent Appeals and Interferences; Apr. 24, 2008.
Declaration of Larry Bogart; Apr. 24, 2008.
Exhibit A of Declaration of Larry Bogart—U.S. Patent No. 5,856,245; Apr. 24, 2008.
Exhibit B of Declaration of Larry Bogart—U.S. Patent No. 5,352,508; Apr. 24, 2008.
Medline Industries, Inc. and Ossur HF Memorandum of Law in Opposition to Molnlycke's Motion for Partial Summary Judgment; Apr. 24, 2008.
Medline Industries, Inc. and Ossur HF Response to Molnlycke Health Care AB and Molnlycke Health Care US Statement of Undisputed Material Facts, and 2. Medline Industries, Inc. and Ossur HF Counter-Statement of Additional Material Facts; Apr. 24, 2008.
Declaration of Jennifer R. Scullion in Support of Medline Industries, Inc. and Ossur HF Opposition to Molnlycke's Motion for Partial Summary Judgment; Apr. 24, 2008.
Exhibit U of Declaration of Jennifer R. Scullion in Support of Medline Industries, Inc. and Ossur HF Opposition to Molnlycke's Motion for Partial Summary Judgment—U.S. Patent No. 5,409,472; Apr. 24, 2008.
Exhibit V of Declaration of Jennifer R. Scullion in Support of Medline Industries, Inc. and Ossur HF Opposition to Molnlycke's Motion for Partial Summary Judgment—U.S. Patent No. 5,571,529; Apr. 24, 2008.
Exhibit W of Declaration of Jennifer R. Scullion in Support of Medline Industries, Inc. and Ossur HF Opposition to Molnlycke's Motion for Partial Summary Judgment—UK Patent Application GB 2 290 031; Apr. 24, 2008.
Exhibit X of Declaration of Jennifer R. Scullion in Support of Medline Industries, Inc. And Ossur Hf Opposition to Molnlycke's Motion for Partial Summary Judgment - U.S. Patent No. 3,972,328; Apr. 24, 2008.
Exhibit Y of Declaration of Jennifer R. Scullion in Support of Medline Industries, Inc. and Ossur HF Opposition to Molnlycke's Motion for Partial Summary Judgment—U.S. Patent No. 5,209,965; Apr. 24, 2008.
Exhibit Z of Declaration of Jennifer R. Scullion in Support of Medline Industries, Inc. and Ossur HF Opposition to Molnlycke's Motion for Partial Summary Judgment—U.S. Patent No. 5,445,604; Apr. 24, 2008.
Exhibit AA of Declaration of Jennifer R. Scullion in Support of Medline Industries, Inc. and Ossur HF Opposition to Molnlycke's Motion for Partial Summary Judgment—U.S. Patent No. 5,098,500; Apr. 24, 2008.
Exhibit BB of Declaration of Jennifer R. Scullion in Support of Medline Industries and Ossur HF Opposition to Molnlycke's Motion for Partial Summary Judgment—U.S. Patent No. 3,364,063; Apr. 24, 2008.
Exhibit CC of Declaration of Jennifer R. Scullion in Support of Medline Industries and Ossur HF Opposition to Molnlycke's Motion for Partial Summary Judgment—U.S. Patent No. 5,782,787; Apr. 24, 2008.
Exhibit LL of Declaration of Jennifer R. Scullion in Support of Medline Industries and Ossur HF Opposition to Molnlycke's Motion for Partial Summary Judgment—US Patent Application 2004/0127839; Apr. 24, 2008.
Exhibit MM of Declaration of Jennifer R. Scullion in Support of Medline Industries and Ossur HF Opposition to Molnlycke's Motion for Partial Summary Judgment—Excerpts from the Jan. 31, 2007 Videotaped Deposition of Tomas Fabo; Apr. 24, 2008.
Exhibit NN of Declaration of Jennifer R. Scullion in Support of Medline Industries and Ossur HF Opposition to Molnlycke's Motion for Partial Summary Judgment—Excerpts from the Aug. 21, 2007 Video Deposition of Tomas Fabo; Apr. 24, 2008.
Exhibit OO of Declaration of Jennifer R. Scullion in Support of Medline Industries and Ossur HF Opposition to Molnlycke's Motion for Partial Summary Judgment—Excerpts from the Videotaped Deposition of Steven Clarson; Apr. 24, 2008.
Exhibit PP of Declaration of Jennifer R. Scullion in Support of Medline Industries and Ossur HF Opposition to Molnlycke's Motion for Partial Summary Judgment—Excerpts from the Videotaped Deposition of Craig Broussard; Apr. 24, 2008.
Exhibit QQ of Declaration of Jennifer R. Scullion in Support of Medline Industries and Ossur HF Opposition to Molnlycke's Motion for Partial Summary Judgment—Excerpts from the Videotaped Deposition of Larry Bogart; Apr. 24, 2008.
Exhibit RR of Declaration of Jennifer R. Scullion in Support of Medline Industries and Ossur HF Opposition to Molnlycke's Motion for Partial Summary Judgment—Excerpts from the Videotaped Deposition of Baldur Baldursson; Apr. 24, 2008.
Exhibit SS of Declaration of Jennifer R. Scullion in Support of Medline Industries and Ossur HF Opposition to Molnlycke's Motion for Partial Summary Judgment—Excerpts from the Videotaped Deposition of Laura Shafer; Apr. 24, 2008.
Exhibit TT of Declaration of Jennifer R. Scullion in Support of Medline Industries and Ossur HF Opposition to Molnlycke's Motion for Partial Summary Judgment—Excerpts from the Deposition of Hilmar Janusson; Apr. 24, 2008.
Exhibit VV of Declaration of Jennifer R. Scullion in Support of Medline Industries and Ossur HF Opposition to Molnlycke's Motion for Partial Summary Judgment—Excerpts from the Oct. 8, 2007 deposition of Bengt Lindquist; Apr. 24, 2008.
Exhibit WW of Declaration of Jennifer R. Scullion in Support of Medline Industries and Ossur HF Opposition to Molnlycke's Motion for Partial Summary Judgment—Excerpts from the Videotaped Deposition of Palmar Gudnason; Apr. 24, 2008.
Exhibit XX of Declaration of Jennifer R. Scullion in Support of Medline Industries and Ossur HF Opposition to Molnlycke's Motion for Partial Summary Judgment—Excerpts from the Feb. 28, 2008 Deposition of Michael Brook; Apr. 24, 2008.
Exhibit YY of Declaration of Jennifer R. Scullion in Support of Medline Industries, Inc. and Ossur HF Opposition to Molnlycke's Motion for Partial Summary Judgment—Excerpts from the Videotaped Deposition of Andrew Martin Reed, Ph. D.; Apr. 24, 2008.
Exhibit ZZ of Declaration of Jennifer R. Scullion in Support of Medline Industries, Inc. and Ossur HF Opposition to Molnlycke's Motion for Partial Summary Judgment—Excerpts from the Video Deposition of Staffan Kuuse; Apr. 24, 2008.
Exhibit CCC of Declaration of Jennifer R. Scullion in Support of Medline Industries and Ossur HF Opposition to Molnlycke's Motion for Partial Summary Judgment—Wound Care Project overview Exhibit No. 78; Apr. 24, 2008.
Exhibit DDD of Declaration of Jennifer R. Scullion in Support of Medline Industries and Ossur HF Opposition to Molnlycke's Motion for Partial Summary Judgment—Medline's Production No. MED 001810 through 001816; Exhibit No. 20; Apr. 24, 2008.
Exhibit LLL of Declaration of Jennifer R. Scullion in Support of Medline Industries and Ossur HF Opposition to Molnlycke's Motion for Partial Summary Judgment—Ossur's Production No. OS 046840 through 046851; Ulman et al., "Silicone Pressure Sensitive Adhesives for Healthcare Applications."; Apr. 24, 2008.
Exhibit MMM of Declaration of Jennifer R. Scullion in Support of Medline Industries and Ossur HF Opposition to Molnlycke's Motion for Partial Summary Judgment—Excerpt from the file for Patent Interference Proceeding No. 102,565; Apr. 24, 2008.
Exhibit NNN of Declaration of Jennifer R. Scullion in Support of Medline Industries and Ossur HF Opposition to Molnlycke's Motion for Partial Summary Judgment—Staffan Areskoug's Deposition Exhibit No. 6; "Design Input AiO-Dressing"; Apr. 24, 2008.
Expert Declaration of Dr. Michael A. Brook in Support of Medline Industries and Ossur HF Opposition to Molnlycke Health Care AB and Molnlycke Health Care US Motion for Partial Summary Judgment ; Apr. 24, 2008.

Exhibit C of Expert Declaration of Dr. Michael A. Brook in Support of Medline Industries and Ossur HF Opposition to Molnlycke Health Care AB and Molnlycke Health Care US Motion for Partial Summary Judgment—Expert Report of Michael A. Brook, Ph. D. on Validity Issues; Apr. 24, 2008.

Declaration of Andrew M. Reed, Ph.D. In Support of Medline Industries and Ossur HF Opposition to Molnlycke Health Care AB and Molnlycke Health Care US Motion for Partial Summary Judgment; Apr. 24, 2008.

Exhibit A of Declaration of Andrew M. Reed, Ph.D. In Support of Medline Industries and Ossur HF Opposition to Molnlycke Health Care AB and Molnlycke Health Care US Motion for Partial Summary Judgment—Curriculum Vitae of Andrew M. Reed; Apr. 24, 2008.

Exhibit B of Declaration of Andrew M. Reed, Ph.D. In Support of Medline Industries and Ossur HF Opposition to Molnlycke Health Care AB and Molnlycke Health Care US Motion for Partial Summary Judgment—Expert Report of Andrew M. Reed, Ph. D.; Apr. 24, 2008.

Molnlycke Health Care Ab and Molnlycke Health Care US Reply Brief to Medline Industries and Ossur HF Opposition to Motion for Partial Summary Judgment that U.S. Patent No. 6,051,747 is Not Invalid; May 23, 2008.

Excerpts of Feb. 1, 2007 Videotaped Deposition of Dr. Steven J. Clarson; May 23, 2008.

Excerpts of Videotaped Deposition of Stefan Areskoug; May 23, 2008.

Excerpts of Mar. 6, 2008 Videotaped Deposition of Dr. Steven J. Clarson (Taken by Medline Industries and Ossur HF); May 23, 2008.

Excerpts of Aug. 21, 2007 Video Deposition of: Mr Tomas Fabo; May 23, 2008.

Exhibit 36 of Molnlycke Health Care AB and Molnlycke Health Care US Reply Brief to Medline Industries and Ossur HF Opposition to Motion for Partial Summary Judgment that U.S. Patent No. 6,051,747 Is Not Invalid; Filed Under Seal Pursuant to Protective Order; May 23, 2008.

Excerpts of Videotaped Deposition of James Wetrich; May 23, 2008.

Excerpts of Videotaped Deposition of Laura Shafer; May 23, 2008.

Excerpts of Videotaped Deposition of Craig Broussard, Ph.D., R.N.; May 23, 2008.

Excerpts of Videotaped Deposition of Larry Bogart; May 23, 2008.

Excerpts of Video Deposition of Staffan Kuuse; May 23, 2008.

Exhibit 42 of Molnlycke Health Care AB and Molnlycke Health Care US Reply Brief to Medline Industries and Ossur HF Opposition to Motion for Partial Summary Judgment that U.S. Patent No. 6,051,747 is Not Invalid; Filed Under Seal Pursuant to Protective Order; May 23, 2008.

Excerpts of Video Deposition of Elisabet Lundqvist; May 23, 2008.

Second Declaration of Larry Bogart; May 23, 2008.

Expert Report of Mr. Larry Bogart dated Dec. 28, 2007; May 23, 2008.

Medline Industries and Ossur Hf Reply Memorandum in Support of Motion for Summary Judgment of Invalidity; May 23, 2008.

Appendix of Unreported Authorities; May 23, 2008.

Excerpts from Manual of Patent Examining Procedure (Jul. 1997 Revisions); May 23, 2008.

Transcript of Videotaped Deposition of Tomas T. Fabo on Jan. 31, 2007 (215 pages); Jan. 31, 2007.

Transcript of Videotaped Deposition of James Wetrich (199 pages); Jan. 31, 2007.

International Search Report dated Mar. 20, 2008, in PCT application.

\* cited by examiner

SILVER-CONTAINING FOAM STRUCTURE

The present invention relates to an antibacterial and hydrophilic polyurethane foam structure. More specifically, the antibacterial and hydrophilic foam structure contains an increased amount of silver both in the polymer matrix and inside the cells of the foam. Furthermore, the invention provides a method for manufacturing said antibacterial and hydrophilic foam structure.

TECHNICAL BACKGROUND

WO 97/42985 discloses a wound dressing comprising a layer of absorbent foam material which includes a pattern of holes. The holes open out on that side of the foam material which lies proximal to the wearer's skin when the dressing is worn, and the layer of foam material is coated with a layer of skin-adhering hydrophobic gel, wherein those end parts of the walls of the holes in the foam material that lie proximal to the wearer's skin when the dressing is worn are gel-coated. Nothing is disclosed about including particular antimicrobial or antibacterial compounds in the dressing.

U.S. Pat. No. 5,662,913 describes using silver salts that are stabilised by forming complexes with acyclic polyether polymers. Furthermore, the anions of the silver salts are present in excess in relation to the silver ions. The stabilised silver salt complexes of U.S. Pat. No. 5,662,913 can be included in foam structures. The object of the invention disclosed in this patent is to provide photo-stable, non-staining antimicrobial metal compositions for protection against infections, and to render a polyurethane-based foam object antimicrobial. Nothing is disclosed about controlling the release of silver from a polyurethane structure.

WO 2004/007595 discloses a flexible cellular polyurethane foam product which has been produced in the presence of a controlled release silver component. The release of silver from the structure is generally slow, which is advantageous in some applications but may not be sufficient in other applications.

EP-A1-1 486 523 and U.S. Pat. No. 4,937,273 both relate to polyurethane foams containing antimicrobial silver bound to zeolite particles. The release of silver from the structure is generally slow, which is advantageous in some applications but may not be sufficient in other applications.

WO 2002/062403 discloses production of wound dressings with releasable silver complexes formed with metals of group IV of the periodic system of elements, and in particular silver zirconium salts. Nothing is disclosed regarding the silver salts in claim 1 of the present application.

EP-A1-0 059 049 relates to wound dressings containing silver sulphadiazine. Nothing is disclosed regarding the silver salts in claim 1 of the present application.

Different wounds require different release patterns for antimicrobial agents, such as silver. For infected wounds and wounds that may become easily infected, it would, however, be desirable to use a dressing which initially would be capable of releasing large amounts of anti-microbial silver and which would be capable of maintaining such a release for a prolonged period of time.

SUMMARY OF THE INVENTION

The present invention provides a method of producing an antibacterial and hydrophilic polyurethane foam structure that can be used as a wound dressing. The method comprises the steps of a) providing a water phase containing a surfactant;
b) providing a isocyanate-terminated polyether having functionality of more than 2;
c) mixing said water phase and said isocyanate-terminated polyether, immediately transferring the resulting mixture to a mould or a continuous web whereby a foam structure is obtained; and
d) drying said foam structure until it has a moisture content of at most 10% (wt), preferably at most 8% (wt), and still more preferably at most 5% (wt).

The essential feature of the method is that the water phase in step a) also contains a silver salt. A part of said silver salt is dispersed in said water phase. The advantage of this method is that antimicrobial silver ions are released from the foam in a favourable manner during a prolonged period of time. The above mentioned silver salt is chosen from the group of silver sulphate, silver citrate, silver acetate, silver carbonate, silver lactate and silver phosphate, or a mixture of these salts.

Furthermore, it is preferred to line said mould or continuous web with casting paper before the mixture is added in step c). Said casting paper is removed before the drying step d).

In the presence of a catalyst, it is also preferred to add one or more gel-forming silicone components, that by curing form a cross-linked silicone gel, to one surface of the foam structure obtained after step d). Said catalyst is preferably a platinum complex.

Finally, the present invention provides an antibacterial and hydrophilic polyurethane foam structure having a pore size between 30 and 1000 µm, wherein said structure can be produced by the above disclosed method. Preferably, the accumulated silver release per $cm^2$ of the foam structure after 48 hours amounts to more than 0.2 $mg/cm^2$, more preferably to more than 0.25 $mg/cm^2$ and most preferably to more than 0.30 $mg/cm^2$. Furthermore, the accumulated silver release per $cm^2$ of the foam structure after 72 hours preferably amounts to more than 0.3 $mg/cm^2$, more preferably to more than 0.35 $mg/cm^2$ and most preferably to more than 0.40 $mg/cm^2$. Preferably, the accumulated silver release amounts to at most 0.80 $mg/cm^2$ after 48 hours, more preferably after 96 hours, and most preferably after 120 hours.

Preferably, the antibacterial characteristics of the foam structure is such that a circular sample of said foam having a diameter of 20 mm and a thickness of 5 mm, when exposed to 10 ml bacteria-containing simulated wound fluid (a 1:1 solution of fetal calf serum and peptone water (aqueous solution containing 0.9% (wt) NaCl and 0.5% (wt) peptone)) at a temperature of 35° C.+/−2° C. according to reference method ASTM E 2149, is able to reduce the amount of viable *Pseudomonas aeruginosa* cells from $10^6$ to less than $10^2$ in 72 hours, and to reduce the amount of viable *Staphylococcus aureus* cells from $10^6$ to less than $10^2$ in 120 hours.

The present invention also provides a wound dressing comprising said silver-releasing foam structure.

DETAILED DESCRIPTION OF THE INVENTION

Accordingly, the present invention provides a method for manufacturing an antibacterial and hydrophilic foam structure showing improved release of antibacterial silver ions over time.

The hydrophilic foam structure of the present invention is basically a hydrophilic polyurethane foam. Suitable hydrophilic polyurethane foams include those known as Hypol (trademark) foams. Hypol foams can be made from Hypol hydrophilic prepolymers marketed by Dow Chemicals.

The conformable hydrophilic polyurethane foam can be made by mixing together an isocyanate terminated polyether having functionality of more than two with a surfactant and water and casting the mixture onto a surface.

Preferred isocyanate terminated polyethers include Hypol FHP 2000, 2001, 3000, 3001, 2002 and 2000HD marketed by Dow Chemicals. Hypol is described in a booklet published by W. R. Grace and Co. "Hypol: foamable hydrophilic polymers—laboratory procedures and foam formulations". Their preparation and use are disclosed in British Patent Specifications Nos. 1429711 and 1507232.

Suitable surfactants for forming conformable hydrophilic polymer foams include non-ionic surfactants. Favored non-ionic surfactants are oxypropylene-oxyethylene block copolymers known as Pluronic (trademark) marketed by BASF Wyandotte. Preferred Pluronic surfactants include L65, F87, P38, P75 and L62.

Suitable sources of silver are silver salts with moderate solubility in water. It is also important that the silver salts are stable at sterilisation conditions and that they are pharmaceutically acceptable. In one embodiment of the invention, silver salts with moderate solubility in water are mixed with silver salts having low water solubility. It is essential that a part of the silver salt is dispersed in the aqueous reaction mixture during the manufacturing process. Examples of silver salts that could be used according to the present invention are found within the group of silver sulphate, silver citrate, silver acetate, silver carbonate, silver lactate and silver phosphate, or a mixture of these salts.

To prepare a typical foam, 100 parts by weight of Hypol FHP 2000, 2001, 3000, 3001, 2002 or 2000HD is mixed with 0.3 to 7 parts by weight of surfactant or mixtures of surfactants, 2 to 9 parts by weight of a silver salt, such as silver sulphate, and 30 to 300 parts by weight of water and the foaming mixture cast onto a surface. Typical foaming mixtures have a cream time of about 20-30 s., a rise time of about 60-250 s. and a cure time of about 400-800 s. Moreover, suitable foam pore sizes may vary between 30 and 1000 μm.

As already mentioned, the antibacterial and hydrophilic polyurethane foam structure of the present invention can on one side be coated with a silicone gel, by adding one or more gel-forming silicone components thereto and allow the added silicone to form a cross-linked gel by curing. The cross-linked silicone gel used as coating of the antibacterial, hydrophilic polyurethane foam of the present invention can conveniently be characterised in terms of its tensile strength, penetrability and peel strength. As the term is used herein, "tensile strength" means the maximum tensile load which can be applied (by means of a standard Instron tester) to a 5 cm wide, 3 mm thick strip of the cross-linked silicone gel in question.

The cross-linked silicone gel may be formed from various gel-forming silicone components and mixtures, such as e.g. from linear silicones having reactive groups thereon, as is known in the art. Preferably, the gels are formed by reaction between a vinyl-substituted silicone component and a hydride-containing silicone component in the presence of a suitable catalyst such as a platinum catalyst.

The gel-forming silicone components used may have a viscosity within the range of 100-10000 mPas, a number average molecular weight in the range 350 to 40,000, and may, for example, have from 0.004 to 0.4 mmoles reactive group/g.

When the silicone gels are formed by cross-linking a mixture of two or more silicone components, the molecular weights of the various components and/or their degree of substitution by reactive groups may be different. This allows gels having different physical properties to be formed merely by varying the proportions of the components.

The components for forming suitable cross-linked silicones for use in the antibacterial, hydrophilic polyurethane foam structure of the present invention are available from e.g. Wacker, under the reference Wacker Silgel 612.

As already mentioned, the structures of the present invention are formed by coating a sheet of foamed material with one or more non-crosslinked silicone components and then causing cross-linking to occur. In the case of gels formed by reacting vinyl groups of one component with hydride groups of the other component, such curing will generally be carried out in the presence of a catalyst such as a platinum complex at a concentration of from 5 to 15 ppm. In such a case, the gel may be formed by curing at room temperature over a period of several days, but elevated temperatures are preferably employed. For example, the silicone gels may be formed by curing at a temperature of from 40° to 120° C. and preferably at a temperature between 80° and 100° C. At a temperature of 80° C., curing will generally take from 10 seconds to 10 minutes, for example from 1 to 5 minutes. At a temperature of 50° C., curing will generally take from 10 minutes to 2 hours, for example from 15 minutes to 1 hour.

One example of chemically suitable gel (polydimethyl, siloxane gel)-forming silicone components is a platinum-catalysed 2-component addition hardening RTV silicone, such as SilGel 612 from Wacker-Chemie GmbH, Burghausen, Germany, and MED-6340 from NuSil Technology, Carpinteria, USA.

Thus, the present invention provides a dressing that is characterized by a layer of absorbent, antibacterial and, hydrophilic silver ion-containing polyurethane foam material that includes a pattern of holes which open into that side of the foam material that lies proximal to the wearer's skin when in use. Preferably, the foam material has a coating of a layer of hydrophilic cross-linked silicone gel which adheres to the skin, and wherein the walls of the holes in the foam material are coated with gel at those end parts of said walls which lie proximal to the wearer's skin when the dressing is used.

In a first preferred embodiment intended for wounds from which fluid is exuded only slightly or in normal quantities, the foam structure has a hole pattern comprised of the pores in the antibacterial foam material. In case a cross-linked silicone gel is applied, said gel also extends slightly into the open pores of the foam material that border on the gel layer, without closing all pores.

Preferably, the foam material is coated with a layer of liquid-impervious material on that side of the foam material that lies distal from the wearer's skin in use.

The dressing comprising the antibacterial foam structure and having a silicone gel coating on the side intended towards the wearers skin has a skin adhesion force F1 of 0.1-2.0 N, suitably 0.2-1.3 N and preferably 0.2-0.7 N.

In a first embodiment the silicone gel layer has a thickness of 0.05-1.0 mm.

In a second embodiment a pattern of holes is created in the foam material before placing said material on the mixture layer of gel-forming silicone components.

The invention will now be described in more detail with reference to the accompanying drawings, in which:

FIG. 4 shows diagrams of silver release comparing the herein presented material (Sample A) with two commercially available silver foams (Sample B as described in WO 2002/062403 and Sample C as described in U.S. Pat. No. 5,681,575 and U.S. Pat. No. 5,837,275). FIG. 4A shows the amount of released silver at specific time points, while

FIG. 5 shows diagrams of the sustained antimicrobial effect of the herein presented invention (Sample A) compared to two other market available silver foam products (Sample B as described in WO 2002/062403 and Sample C as described in U.S. Pat. No. 5,681,575 and U.S. Pat. No. 5,837,275). FIG. 5A shows the effect on *Staphylococcus aureus* and FIG. 5B shows the effect on *Pseudomonas aeruginosa*. For both bacteria types, the antibacterial foam obtained by the herein presented invention shows a higher antimicrobial, i.e. antibacterial efficiency than the reference samples.

Figure 6:
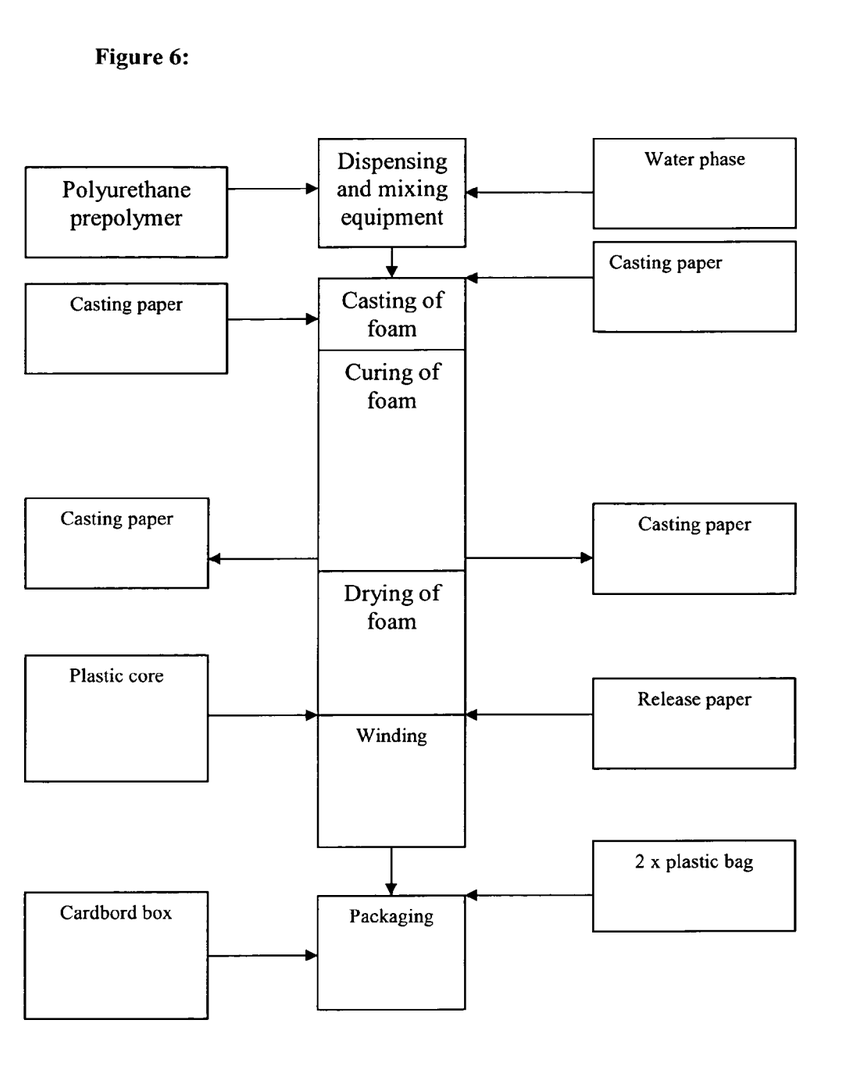
FIG. 6 outlines the manufacturing of a dressing containing a structure according to the present invention. Shown is the manufacturing of silver foam. The water phase contains water, a silver salt such as silver sulphate, and surfactants.

FIG. 6 describes the manufacturing process. Polyurethane prepolymers are mixed with a water phase containing surfactants, a dispersed and dissolved silver salt in a dispensing and mixing equipment. The reaction mixture is subsequently transferred to a mould or a continuous web that has been lined with casting paper. After the termination of the polymerisation reaction, the casting paper is removed from the castings and the obtained foam is dried to a moisture content of at most 10% (wt), preferably at most 8% (wt), most preferably at most 5% (wt). The foam is then rolled on plastic cores with a paper in-between the layers and packaged.

Figure 1:
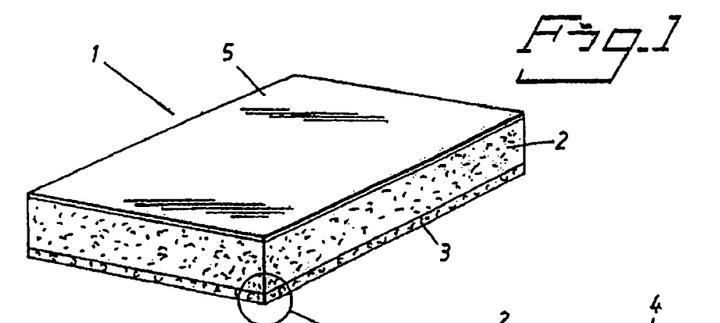
FIG. 1 is a schematic perspective view of a piece of an inventive dressing according to one embodiment.
Figure 1A:
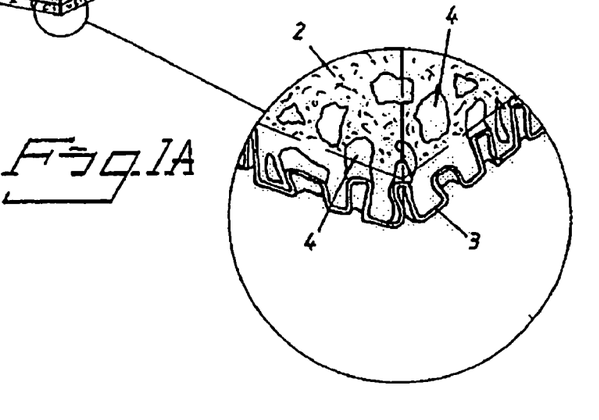
FIG. 1A is an enlarged view of one feature of the FIG. 1 illustration.

FIG. 1 illustrates a piece of a dressing according to one embodiment of the invention. The dressing is comprised of an absorbent foam material 2 which is coated with a gel layer 3 on that side which lies proximal to the wound or skin of the wearer when the dressing is used. As illustrated schematically in FIG. 1A, the gel layer 3 is disposed so that even a part of the walls of the open cells or pores 4 in the foam material that open into the gel-coated side thereof are gel coated. Because the gel layer 3 does not close, but only covers, a part of the walls in an end portion of the pores of the foam material that face the wound, excess wound fluid can be drawn into the foam material 2 and absorbed thereby. The gel layer also forms a spacing layer which prevents the foam material from coming into direct contact with the wound or skin of the wearer. The thickness of the total gel layer, i.e. including the depth of penetration into the pores of the foam material, is 0.1-2.0 mm. Some of the pores in the foam material that face towards the wound are closed by the gel layer.

With the intention of providing a dressing that has a dry outer surface, the dressing is given a liquid-impervious layer 5 on the side opposite to the gel layer 3. This liquid-impervious layer may conveniently comprise a thin liquid-impervious, but vapour-permeable, plastic film, for instance a polyurethane film.

The dressing illustrated in FIG. 1 is intended to be used with wounds that exude fluid in quantities ranging from slight to normal. The foam layer has a thickness of 1-10 mm, preferably 2-6 mm. As mentioned before, the foam material functions both as an absorbent and as a gel carrier, and the dressing as a whole will therefore be very soft and pliant. Because the gel adheres to the skin surrounding the wound, the dressing will be held in place while the gel affords a sealing function and prevents maceration, i.e. prevents wound fluid from running over healthy skin and softening and eventually damaging the epidermis. The open structure of the gel layer and the foam material also enables the skin to breathe. The nature of the adhesive gel used in this invention differs totally from the nature of glues that are typically used to secure dressings, for instance the acrylate glues or the hot melt glues that are used today to this end. The significant difference between these glues and the gel used in accordance with the invention is that the gel is much softer and has a better "wetting ability" than said glues. This enables the gels to be given a much lower specific adhesiveness, i.e. lower adhesion per unit of contact surface area, than the specific adhesiveness that must be given to harder glues in order to achieve an equally effective total adhesion as that offered by the gel.

Figure 2:
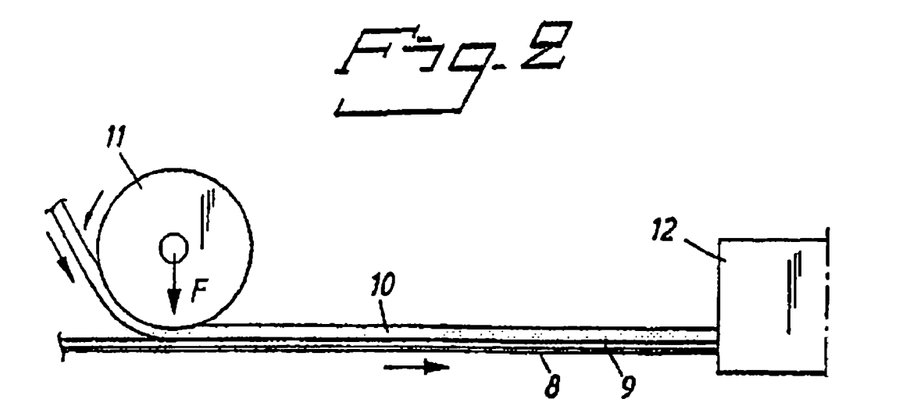
FIG. 2 schematically illustrates an apparatus for applying one or more gel-forming silicone components to a foam structure to obtain a silicone gel coating according to the present invention.

FIG. 2 is a highly schematic illustration of an apparatus for use in applying a layer of one or more gel-forming silicone components to a structure according to the present invention. The illustrated apparatus includes a conveyer (not shown) on which a plastic film 8 is conveyed from left to right in FIG. 2. A layer of uncured gel mixture 9 is placed on the film 8. By gel mixture is meant a mixture of those components which form a gel after curing, including polymers that can react with one another to form a cross-linked structure. A layer 10 of absorbent foam material is applied to the layer 9 of uncured gel mixture with the aid of a roller 11, and the layers 9, 10 are then transported into an oven 12. The gel mixture is cured in its passage through the oven 12 and forms a gel layer on the underside of the foam material.

It has been found that with suitable selection of the one or more gel-forming components and mixtures and proportions thereof, pressure force F, quantity of gel mixture, time between applying foam material and heating the layers, curing temperature, and so on, there will be formed a discontinuous gel coating on the foam material. This is because the gel mixture is drawn by capillary action into those pores or holes in the foam material that open out in that side of the foam material which lies in abutment with the gel mixture. When applying a gel-forming coating to foam material that lacks holes other than pores, the gel mixture must be applied in a layer of such thinness as to ensure that an excessively large number of the pores opening into the underside of the foam material will not be clogged or blocked by the gel coating. The viscosity of the gel mixture and the size of the pores in the foam material also influence the tendency of the mixture to penetrate into the pores. It has been found that the gel mixture layer should preferably be applied at a thickness of 0.05-1.00 mm. A larger part of the gel mixture layer is sucked into the foam, wherewith the total gel layer, including air and foam, will have a thickness of 0.10-2.00 mm.

In a first application of the above method for coating the underside of an antibacterial polyurethane foam sheet with silicone gel, there was used an open cell, soft hydrophilic polyurethane foam sheet having a density of 80-150 kg/m$^3$ and a thickness of 5 mm.

The silicone mixture was prepared from SilGel 612 obtained from Wacker, in an A-component and B-component mixing ratio of 1.0:0.9. The uncured mixture had a viscosity of about 1000 mPa.

The polyurethane sheet was placed on a silicone mixture having a thickness of 0.2 mm, without applying pressure F from the roller 11, in other words the silicone mixture was subjected solely to the weight of the foam sheet. The time taken to transport the foam material 10 and the underlying silicone mixture 9 from the roller 11 to the oven 12 was one minute and the curing temperature was 130° C. The silicone cured in an oven residence time of minutes. A polyurethane film of high vapor permeability and a thickness of 0.025 mm was then firmly glued to the foam on the side thereof opposite to the gel coating. At this mixture ratio, the silicone gel had a penetration number of 16 mm, and the skin adhesion force of the dressing was measured as 0.42 N. Under these conditions, it has been found that the gel mixture layer will preferably have a thickness of at least 0.1 mm, so as to obtain a suitable discontinuous gel coating on the foam material.

When the thickness of the gel mixture layer was greater than 0.4 mm, an excessively large percentage of the pores in the foam material became blocked, resulting in insufficient permeability of the gel coating.

It will be evident from the aforegoing that when carrying out the method described with reference to FIG. 2, the quality of the end product will depend on many factors. It is therefore not possible to provide these factors with general limit values, and such limit values must be established empirically with respect to the gel mixture and the foam material used.

The described method thus enables a dressing of the kind described with reference to FIG. 1 to be produced very easily. The method is also very flexible and enables dressings of mutually different absorbencies to be produced in principle by the same way and with the aid of the same apparatus.

The described dressing can, of course, be sterilized, e.g. by ethylene oxide sterilization or steam sterilization, and is intended for delivery in different sizes and for different types of wounds, both sterile packed and non-sterile packed. Because of their softness, they are suitable for use in combination with compression bandages and can be used beneficially on blisters, leg ulcers and like wounds. Their high degree of flexibility also makes them suitable for use on joint sores, such as knee sores and elbow sores, even in later phases of the sore healing process. The dressings can also be cut to a size suitable for the size of the sore or wound in question.

It will be understood that the above described exemplifying embodiments can be modified within the scope of the invention, particularly with respect to the described materials and process parameters applied.

The invention will now be further described in the enclosed examples.

Example 1

Preparation of the Foam Structure

A water phase for the foam-manufacturing process was prepared by dissolving/dispersing the non-ionic surfactant Pluronic F87, silver sulphate, and active carbon. The final concentrations of these constituents in the water phase amounted to 0.5% (wt) of Pluronic F87, and 2.2% (wt) of silver sulphate. The concentration of dissolved silver sulphate amounted to 0.8% (wt) and the rest of the silver sulphate was dispersed in the water phase.

Simultaneously, a mould lined with casting paper was prepared. The mould had a sufficient depth so that sheet-formed foam castings having a thickness of 5 mm could be produced.

The pre-polymer Hypol 2001 (a isocyanate-terminated polyether) was added to the water phase in a dispensing and mixing equipment in an amount of 40% (wt) at room temperature. The resulting mixture was immediately transferred to the casting mould. The foaming amounted to 30 s, and then the foam was cured for 10 minutes. After curing, the casting papers were removed and the foam was dried to a moisture content of at most 10% (wt) at a temperature of 120° C. (See FIG. 1 and FIG. 2.)

Example 2

Absorption of the Foam Material

Samples of the foam product produced in Example 1, Sample A, and two commercially available products, Sample B as described in WO2002062403 and Sample C as described in U.S. Pat. No. 5,681,575(A) and U.S. Pat. No. 5,837,275 (A), were cut into 6×6 cm test pieces and weighed. Subsequently, the test pieces were soaked in an excess amount of tap water. After three hours, the pieces were re-weighed. The results obtained are shown in Table 1:

TABLE 1

|  | Dry weight (g) | Wet weight (g) | Absorption (g/36 cm$^2$) | Absorption (g/cm$^2$) |
| --- | --- | --- | --- | --- |
| Sample A | 2.82 | 35.5 | 32.7 | 0.91 |
| Sample B | 3.52 | 28.5 | 25.0 | 0.69 |
| Sample C | 3.31 | 33.0 | 29.7 | 0.82 |

The results show that the product of Example 1 (Sample A) has an as good or slightly better absorption capacity as commercially available products.

Example 3

Silver Release

Figure 3:
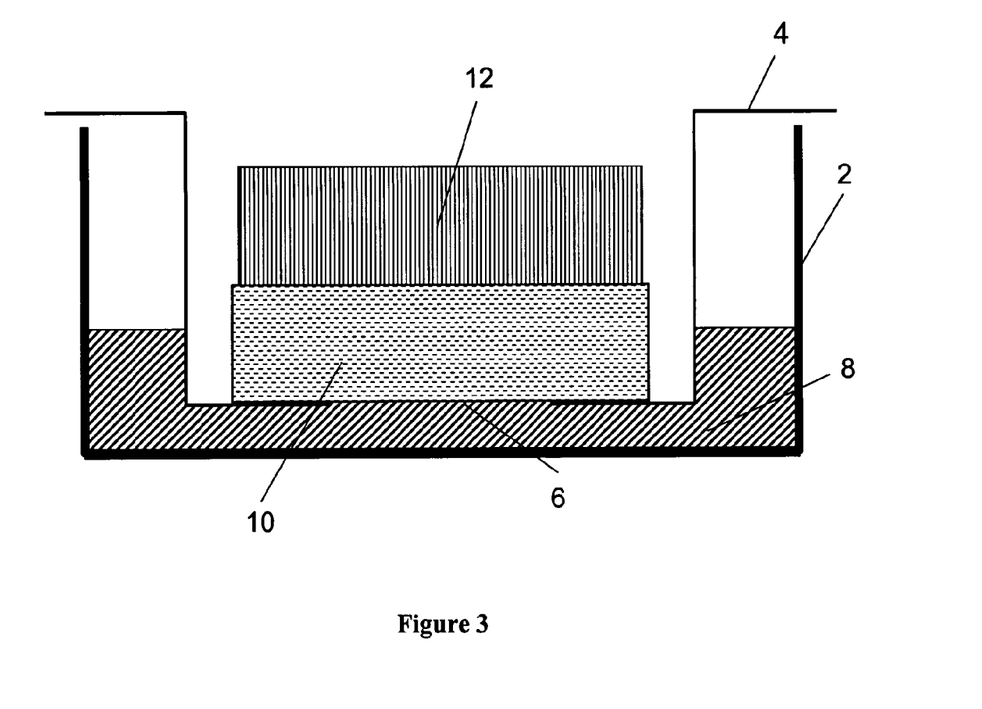
FIG. 3 schematically outlines how silver release from a silver-containing structure is measured.

Circular samples having a diameter of 20 mm were punched out from the material produced according to Example 1, here referred to as Sample A, and two commercially available products, Sample B as described in WO2002062403 and Sample C as described in U.S. Pat. No. 5,681,575(A) and U.S. Pat. No. 5,837,275(A). FIG. 3 discloses some of the equipment for measuring silver release, namely a Falcon™ 6 well Multiwell unit (2) and a corresponding cell culture insert both from Becton Dickinson Labware (4) (The diffusion membrane in the bottom of the cell culture insert (4) was removed and replaced by a waterproof polyamide film. An opening (6) having a diameter of 12 mm was punched out from the bottom film. The dry sample (10) was placed in cell culture insert (4) on top of the opening (6). A weight (12) made of stainless steel, weighing 15 g and having a diameter of 20 mm was arranged on top of the sample (10) in order to compress and fix said sample to the bottom film.

A defined amount of an aqueous 0.15 M solution of NaNO$_3$ (from now on referred to as test solution (8)) was added to the Multiwell™ unit (2) according to the following scheme (table 2):

TABLE 2

| 0 h | 6 h | 24 h | 48 h | 72 h | 96 h | 120 h | 144 h | 168 h |
| --- | --- | --- | --- | --- | --- | --- | --- | --- |
| 3.5 ml | 1.5 ml | 1.5 ml | 1.5 ml | 1.5 ml | 1.5 ml | 1.5 ml | 1.5 ml | 0 ml |

The cell culture insert (4) was placed in the Multiwell™ unit (2), thereby enabling contact between the test solution (8) and the sample (10). The lid of the two-compartment model was applied. At each sampling time, the test solution that had not been absorbed by the sample (10) was collected. After each sampling time, new fresh test solution was added to a clean Multiwell™ unit, wherein the cell culture insert (4), still carrying the same specimen (10) was placed. All six samples were tested as triplicates during the whole test. At each sampling time, the released amount of silver was evaluated with a silver ion electrode.

| Sample | 0 h mg Ag/cm$^2$ | 0 h accumulated mg Ag/cm$^2$ | 6 h mg Ag/cm$^2$ |
|---|---|---|---|
| A | 0 | 0 | 0.006 |
| B | 0 | 0 | 0.005 |
| C | 0 | 0 | 0.002 |

| Sample | 6 h accumulated mg Ag/cm$^2$ | 24 h mg Ag/cm$^2$ | 24 h accumulated mg Ag/cm$^2$ |
|---|---|---|---|
| A | 0.006 | 0.134 | 0.14 |
| B | 0.005 | 0.010 | 0.015 |
| C | 0.002 | 0.005 | 0.007 |

| Sample | 48 h mg Ag/cm$^2$ | 48 h accumulated mg Ag/cm$^2$ | 72 h mg Ag/cm$^2$ |
|---|---|---|---|
| A | 0.18 | 0.32 | 0.15 |
| B | 0.002 | 0.017 | 0.010 |
| C | 0.010 | 0.017 | 0.020 |

| Sample | 72 h accumulated mg Ag/cm$^2$ | 96 h mg Ag/cm$^2$ | 96 h accumulated mg Ag/cm$^2$ |
|---|---|---|---|
| A | 0.47 | 0.13 | 0.60 |
| B | 0.027 | 0.010 | 0.037 |
| C | 0.037 | 0.014 | 0.051 |

| Sample | 120 h mg Ag/cm$^2$ | 120 h accumulated mg Ag/cm$^2$ | 144 h mg Ag/cm$^2$ |
|---|---|---|---|
| A | 0.09 | 0.69 | 0.07 |
| B | 0.014 | 0.051 | 0.010 |
| C | 0.014 | 0.065 | 0.010 |

| Sample | 144 h accumulated mg Ag/cm$^2$ | 168 h mg Ag/cm$^2$ | 168 h accumulated mg Ag/cm$^2$ |
|---|---|---|---|
| A | 0.76 | 0.07 | 0.83 |
| B | 0.061 | 0.010 | 0.071 |
| C | 0.075 | 0.08 | 0.083 |

Figure 4A:
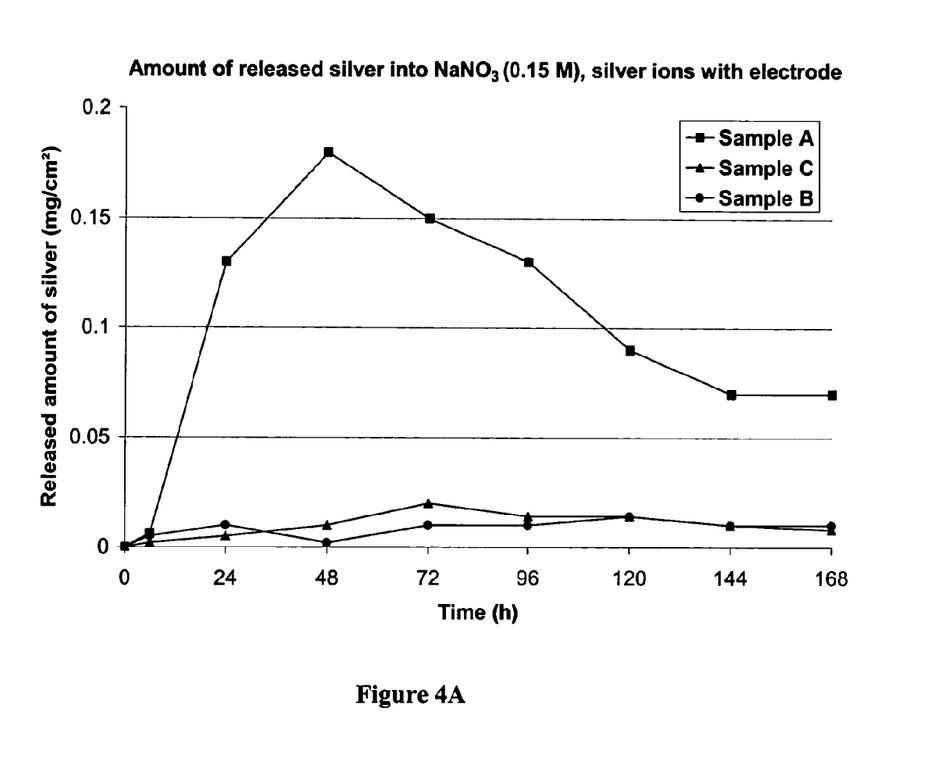
Figure 4B:
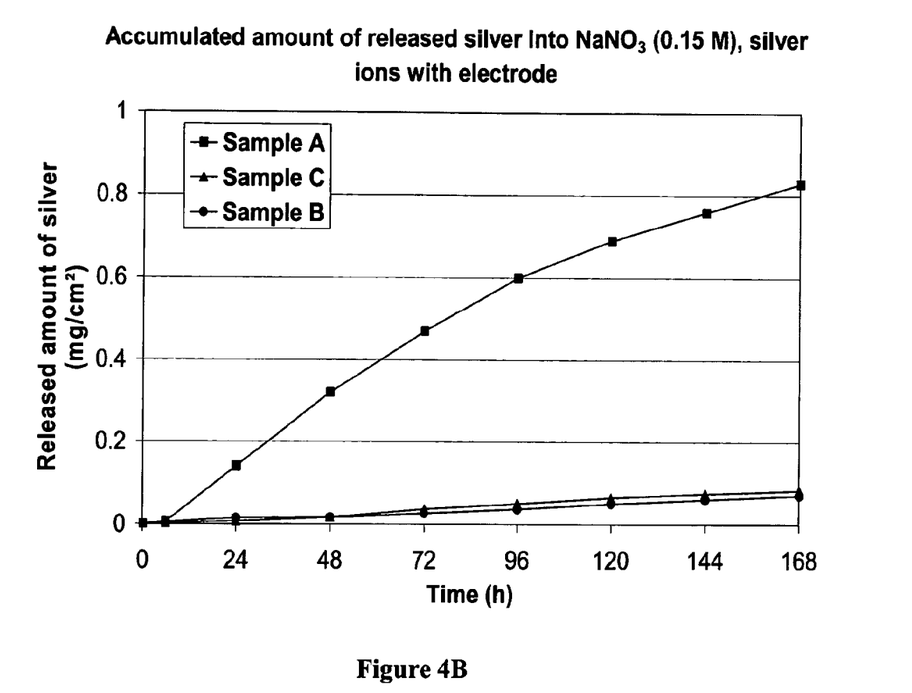
FIG. 4B shows the accumulated silver release.

The obtained results are disclosed in FIGS. 4A and 4B. The product of Example 1 releases about 70% of its silver content during a test period of one week. The highest release rate is obtained after about 48 hours.

Example 4

Antibacterial Activity

The antibacterial activity was measured using a method based on the reference method ASTM E 2149. Samples (20 mm in diameter) of the silver foam as derived in Example 1 (Sample A) and reference material (Sample B as described in WO2002062403, Sample C as described in U.S. Pat. No. 5,681,575(A) and U.S. Pat. No. 5,837,275(A) and a control sample; a foam as described in Example 1 but without any silver content) were placed in flasks with bacteria (*Staphylococcus aureus* or *Pseudomonas aeruginosa*) and 10 ml of simulated wound fluid (SWF), i.e. a 1:1 solution of Fetal Calf Serum and Peptone Water (0.9% NaCl with 0.5% peptone). The flasks were shaken for about 10 seconds and thereafter the flasks were incubated at 35+/−2° C. In order to measure the antimicrobial effect of the products, samples were taken out after every 24 hours up to 8 days. The number of viable cells in the samples was determined by using standard plate count method.

Figure 5A:
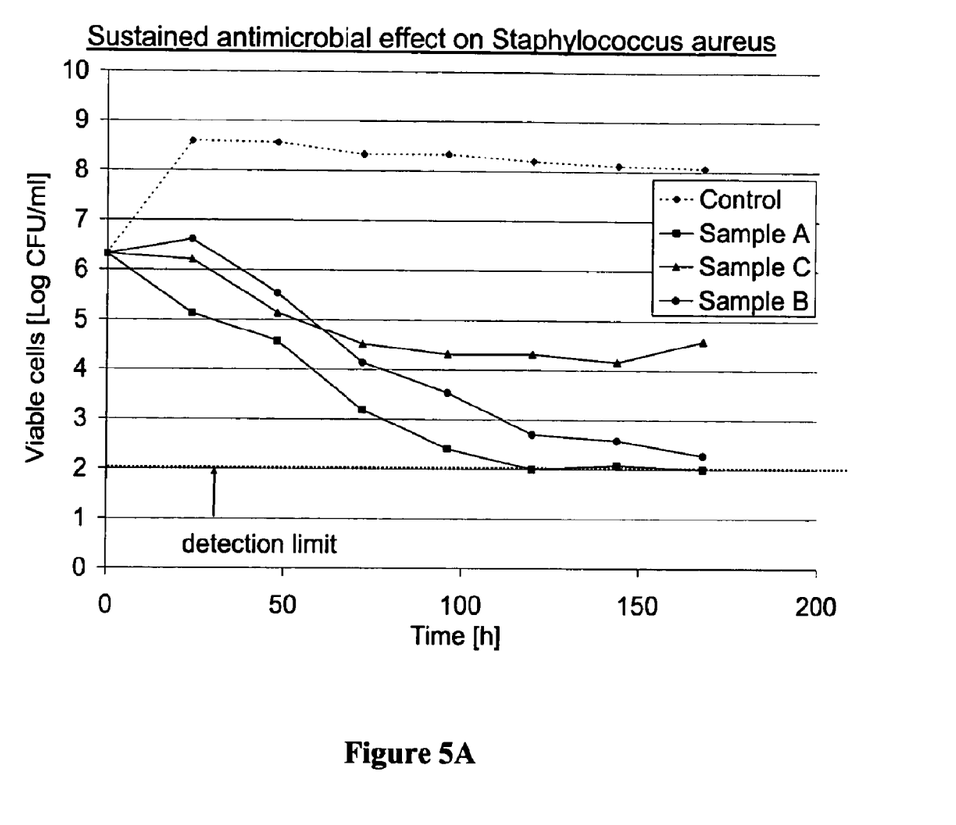
Figure 5B:
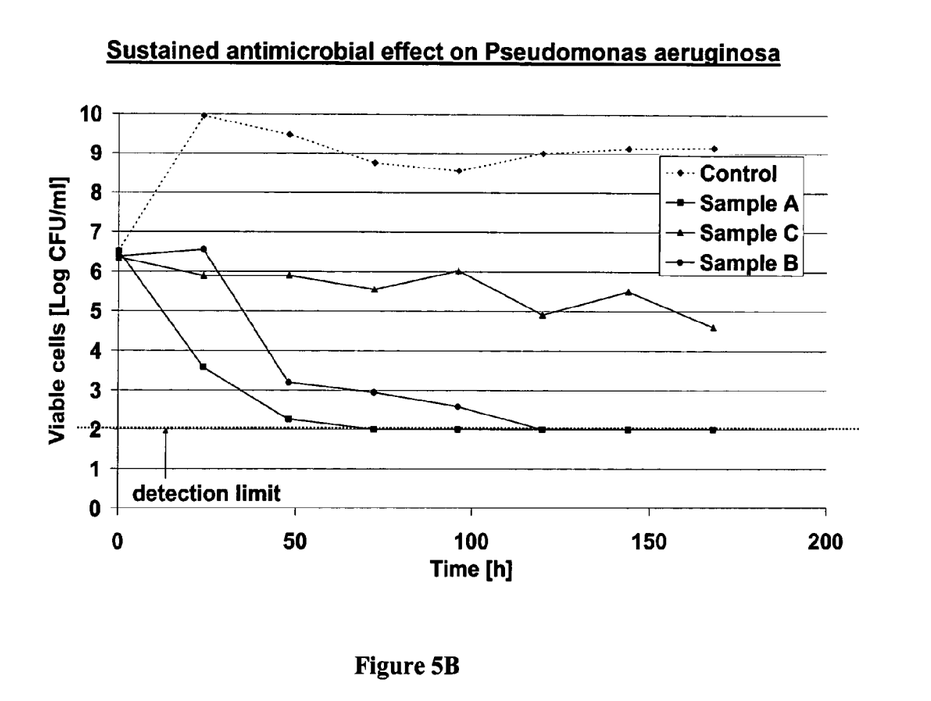

The results from this experiment show a greater reduction of the viable count for *Staphylococcus aureus* by the herein presented silver foam than the other products tested (see FIG. 5A). Reduction of viable count of *Pseudomonas aeruginosa* by Mepilex Ag was also greater than for the other products (see FIG. 5B). The results are also disclosed in Tables 4A and 4B.

TABLE 4A

Sustained antimicrobial effect on *Staphylococcus aureus*

| Sample | 0 h log CFU/ml | 24 h log CFU/ml | 48 h log CFU/ml | 72 h log CFU/ml | 96 h log CFU/ml | 120 h log CFU/ml | 144 h log CFU/ml | 168 h log CFU/ml |
|---|---|---|---|---|---|---|---|---|
| Control | 6.3 | 8.6 | 8.6 | 8.3 | 8.3 | 8.2 | 8.1 | 8.1 |
| Sample A | 6.3 | 5.1 | 4.6 | 3.2 | 2.4 | 2.0 | 2.1 | 2.0 |
| Sample B | 6.3 | 6.6 | 5.5 | 4.1 | 3.5 | 2.7 | 2.6 | 2.3 |
| Sample C | 6.3 | 6.2 | 5.1 | 4.5 | 4.3 | 4.3 | 4.2 | 4.6 |

TABLE 4B

Sustained antimicrobial effect on *Pseudomonas aeruginosa*

| Sample | 0 h log CFU/ml | 24 h log CFU/ml | 48 h log CFU/ml | 72 h log CFU/ml | 96 h log CFU/ml | 120 h log CFU/ml | 144 h log CFU/ml | 168 h log CFU/ml |
|---|---|---|---|---|---|---|---|---|
| Control | 6.52 | 9.95 | 9.48 | 8.75 | 8.55 | 9.00 | 9.13 | 9.15 |
| Sample A | 6.51 | 3.58 | 2.26 | 2.00 | 2.00 | 2.00 | 2.00 | 2.00 |
| Sample B | 6.38 | 6.55 | 3.20 | 2.95 | 2.59 | 2.00 | 2.00 | 2.00 |
| Sample C | 6.35 | 5.89 | 5.90 | 5.55 | 6.03 | 4.90 | 5.49 | 4.59 |

The detection limit is 2.00 log CFU/ml.

The invention claimed is:

1. A method of producing an antibacterial and hydrophilic polyurethane foam structure comprising the steps of
   a) providing a water phase comprising a surfactant and a silver salt, wherein the silver salt comprises silver sulphate, silver citrate, silver acetate, silver carbonate, silver lactate, or silver phosphate, or a mixture thereof, and wherein a part of the silver salt is dispersed in the water phase;
   b) providing an isocyanate-terminated polyether having a functionality of more than 2;
   c) mixing said water phase and said isocyanate-terminated polyether, and immediately transferring the resulting mixture to a mould wherein the hydrophilic polyurethane foam structure is formed in the mould; and
   d) drying said foam structure, wherein the dried foam structure has a moisture content of at most 10% by weight.

2. The method of claim 1, wherein said mould is lined with casting paper before step c) and wherein said casting paper is removed before step d).

3. The method of claim 2, wherein the method further comprises adding one or more gel-forming silicone components to one surface of the hydrophilic polyurethane foam structure obtained after step d) in the presence of a catalyst, wherein said gel-forming components form a cross-linked silicone gel by curing.

4. The method of claim 1, wherein the method further comprises adding one or more gel-forming silicone components to one surface of the hydrophilic polyurethane foam structure obtained after step d) in the presence of a catalyst, wherein said gel-forming components form a cross-linked silicone gel by curing.

5. The method of claim 4, wherein said catalyst comprises a platinum complex.

6. The method of claim 1, wherein the dried hydrophilic polyurethane foam structure has at most 8% moisture content by weight.

7. The method of claim 1, wherein the dried hydrophilic polyurethane foam structure has at most 5% moisture content by weight.

* * * * *